(12) United States Patent
Boyd et al.

(10) Patent No.: US 9,801,594 B2
(45) Date of Patent: Oct. 31, 2017

(54) EBEAM TOMOSYNTHESIS FOR RADIATION THERAPY TUMOR TRACKING

(71) Applicant: Imatrex Inc., Las Vegas, NV (US)

(72) Inventors: Douglas P. Boyd, Las Vegas, NV (US);
Samuel M. Song, Las Vegas, NV (US);
Roy E. Rand, Portola Valley, CA (US);
Larry Partain, Los Altos, CA (US);
Junghyun Kwon, Las Vegas, NV (US)

(73) Assignee: Imatrex Inc., Las Vegas, NV (US)

( * ) Notice: Subject to any disclaimer, the term of this patent is extended or adjusted under 35 U.S.C. 154(b) by 0 days.

(21) Appl. No.: 14/288,021

(22) Filed: May 27, 2014

(65) Prior Publication Data

US 2014/0348288 A1 Nov. 27, 2014

Related U.S. Application Data

(60) Provisional application No. 61/827,359, filed on May 24, 2013.

(51) Int. Cl.
*A61N 5/10* (2006.01)
*A61B 6/03* (2006.01)
(Continued)

(52) U.S. Cl.
CPC .............. *A61B 6/405* (2013.01); *H01J 35/14* (2013.01); *H01J 35/30* (2013.01); *H01J 37/147* (2013.01);
(Continued)

(58) Field of Classification Search
CPC .... H05G 1/52; A61B 6/00; A61B 6/03; A61B 6/032; A61B 6/035; A61B 6/40; A61B 6/4021; A61B 6/4028; A61B 6/405; A61B 34/00; A61B 34/20; A61B 2034/2046; H01J 35/00; H01J 35/02; H01J 35/14; H01J 35/24; H01J 35/30; H01J 37/00; H01J 37/02; H01J 37/04; H01J 37/06; H01J 37/065; H01J 37/147; H01J 37/1471; H01J 37/1472; H01J 37/1474; H01J 37/1475; H01J 37/1477; A61N 5/00; A61N 5/01;
(Continued)

(56) References Cited

U.S. PATENT DOCUMENTS 5,233,990 A * 8/1993 Barnea ..................... A61B 6/00
378/65
7,936,858 B2 5/2011 Hashemi et al.
(Continued)

*Primary Examiner* — Anastasia Midkiff
(74) *Attorney, Agent, or Firm* — Workman Nydegger

(57) ABSTRACT

A system for tracking tumors during radiotherapy by interleaving treatment pulses with imaging pulses is disclosed. The system includes a multisource scanning eBeam X-ray tube having a plurality of focal spots. The X-ray tube is configured to emit X-rays to a plurality of different locations on a target by sequentially emitting the X-rays to the focal spots in the plurality of focal spots. This is done such that the X-rays can be emitted to the plurality of different locations on the target without substantially moving the X-ray tube or the target. The system further includes an imager panel configured to act as the target and configured to receive the X-rays from the focal spots of the X-ray tube. The system further includes a tomosynthesis reconstruction module configured to process output from the imager panel to construct an image.

19 Claims, 8 Drawing Sheets

(51) Int. Cl.
    *H01J 35/14* (2006.01)
    *H01J 35/30* (2006.01)
    *H05G 1/52* (2006.01)
    *A61B 6/00* (2006.01)
    *H01J 37/147* (2006.01)
    *A61B 6/02* (2006.01)
    *A61N 5/06* (2006.01)

(52) U.S. Cl.
    CPC ............... *H05G 1/52* (2013.01); *A61B 6/025* (2013.01); *A61B 6/541* (2013.01); *A61B 6/542* (2013.01); *A61N 5/1048* (2013.01); *A61N 5/1049* (2013.01); *A61N 2005/0632* (2013.01); *A61N 2005/1061* (2013.01)

(58) Field of Classification Search
    CPC ...... A61N 5/10; A61N 5/1042; A61N 5/1048; A61N 5/1049; A61N 5/1064; A61N 5/1065; A61N 5/1067; A61N 5/1077; A61N 5/1084; A61N 2005/0626; A61N 2005/0629; A61N 2005/0632; A61N 2005/1061; A61N 2005/1092
    USPC ....... 378/11, 12, 91, 98, 98.6, 113–115, 119, 378/121, 124, 137, 143, 145, 146, 204, 378/205, 210; 250/396 R, 397, 398, 250/522.1
    See application file for complete search history.

(56) References Cited

U.S. PATENT DOCUMENTS

| | | | |
|---|---|---|---|
| 8,515,004 B2 | 8/2013 | Star-Lack et al. | |
| 8,530,849 B2 | 9/2013 | Boyd et al. | |
| 2007/0081623 A1* | 4/2007 | Eilbert | G01N 23/2252 378/10 |
| 2009/0080604 A1* | 3/2009 | Shores | A61B 6/032 378/37 |
| 2010/0166144 A1* | 7/2010 | Boyd | A61N 5/1049 378/62 |
| 2011/0080990 A1* | 4/2011 | Filiberti | A61N 5/1049 378/4 |
| 2012/0163531 A1* | 6/2012 | Zhang | A61B 6/025 378/9 |
| 2012/0230462 A1* | 9/2012 | Robar | A61N 5/1049 378/4 |
| 2012/0300901 A1* | 11/2012 | Lewalter | A61B 6/4028 378/22 |

\* cited by examiner

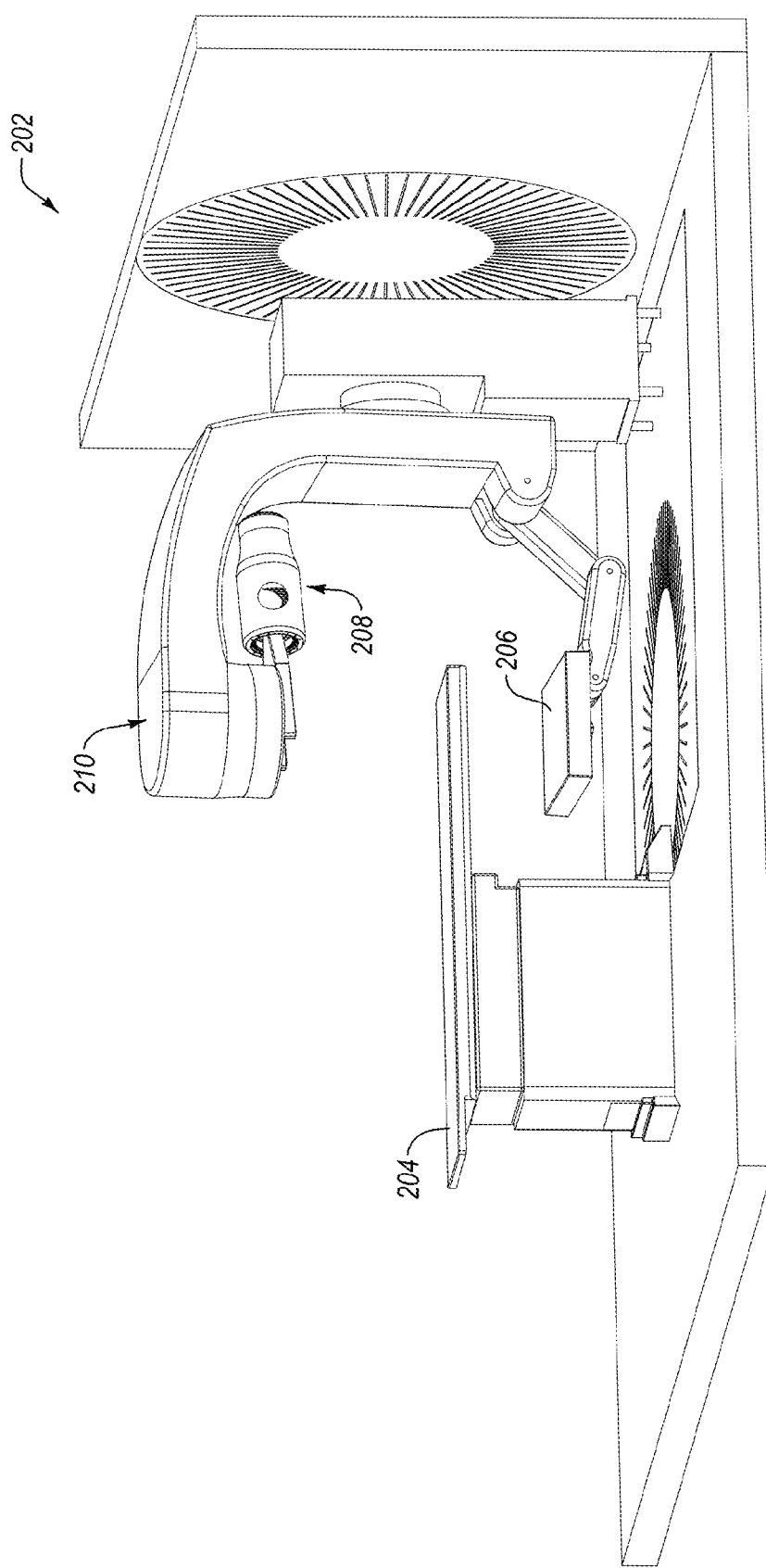

| Acquire 19 kV Projection Images (kV) (40 ms readout + dwell of 7ms each) (0.89s) | Deliver MV Treatment Pulses (0.96s) | Reset For kV Imaging (0.07s) |
|---|---|---|

1.92 s Cycle Time (0.52cycles/s)

EBEAM TOMOSYNTHESIS FOR RADIATION THERAPY TUMOR TRACKING

CROSS-REFERENCE TO RELATED APPLICATIONS

This application claims the benefit of and priority to U.S. Provisional Patent Application Ser. No. 61/827,359 filed on May 24, 2013 and entitled "EBEAM TOMOSYNTHESIS FOR RADIATION THERAPY TUMOR TRACKING," which application is expressly incorporated herein by reference in its entirety.

BACKGROUND

Background and Relevant Art

Lung cancer is a major health problem. Every year, more people in the U.S. die from lung cancer than from prostate, breast, colon and rectum cancers combined. Stereotactic body radiation therapy (SBRT) is a highly successful non-invasive alternative to surgery for localized lung tumors, with local control rates reported to be 80% to 90%. Early reports of high normal tissue toxicities following SBRT (i.e. normal healthy tissue being exposed to tissue destroying radiation) have led to empirically-derived limits on radiation dose metrics and target size. However, these restrictions limit the number of patients that are eligible for SBRT. Often, the tumor itself is small enough for safe treatment, but the treated volume exceeds the safely treatable limit due to the addition of clinical safety margins to account for random and systematic motions. In addition, recent studies have shown that lung tumor motion during radiotherapy cannot be reliably predicted from pretreatment imaging. Direct in-treatment imaging of lung tumors to ensure proper radiation targeting and healthy tissue avoidance is an unsolved challenge.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

One embodiment illustrated herein includes a method that includes acts for tracking tumors during radiotherapy for interleaving treatment pulses with imaging pulses. The method includes emitting eBeam X-rays to a plurality of focal spots on an X-ray tube to emit X-rays in a plurality of different locations on a target by sequentially emitting the X-rays to the focal spots in the plurality of focal spots. This is done such that the X-rays can be emitted to the plurality of different locations without substantially moving the X-ray tube or the target. The method further includes detecting signals from the X-rays at the target. Using the signals, an image is constructed.

Another embodiment includes a system for tracking tumors during radiotherapy for interleaving treatment pulses with imaging pulses. The system includes a multisource scanning eBeam X-ray tube having a plurality of focal spots. The X-ray tube is configured to emit X-rays in a plurality of different locations on a target by sequentially emitting the X-rays to the focal spots in the plurality of focal spots. This is done such that the X-rays can be emitted to the plurality of different locations without substantially moving the X-ray tube or the target. The system further includes an imager panel configured to act as the target and configured to receive the X-rays from the focal spots of the X-ray tube. The system further includes a tomosynthesis reconstruction module configured to process output from the imager panel to construct an image.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which:

FIG. 2A illustrates an example of a radiotherapy system.

DETAILED DESCRIPTION

Figure 1A:
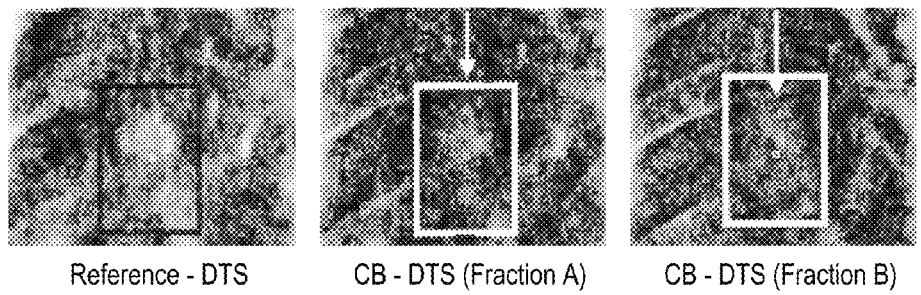
FIG. 1A illustrates shifting of a tumor.
Figure 1B:
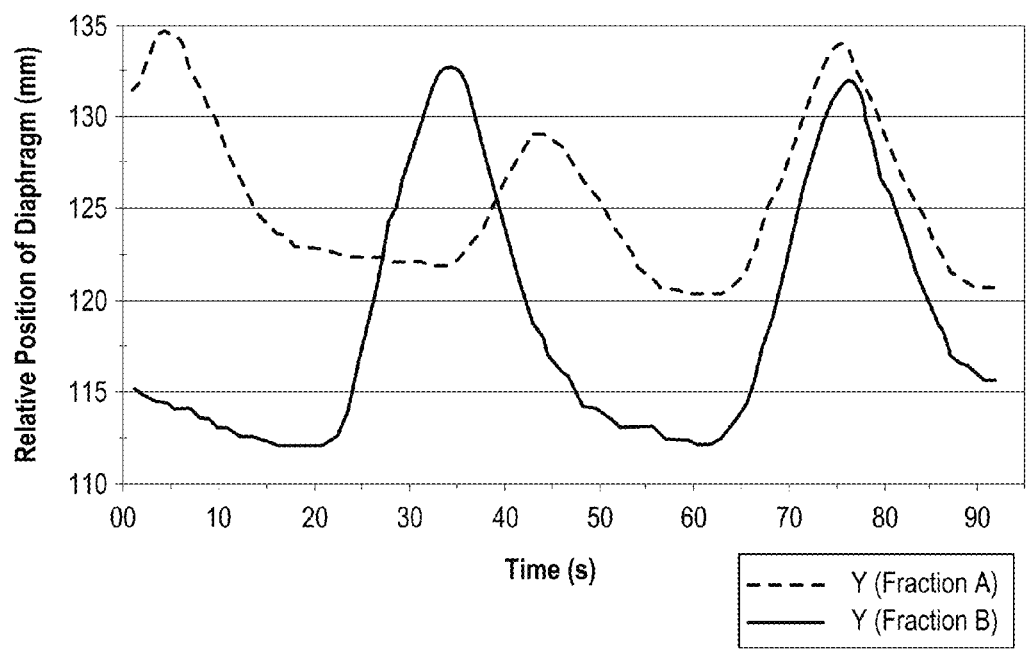
FIG. 1B illustrates a graph showing diaphragm motion.

Embodiments of the invention may implement methods and/or systems for achieving synchronized image guided stereotactic body radiation therapy (SIG-SBRT) or synchronized image guided stereotactic ablative radiotherapy (SIG-SABR). Here SIG-SBRT and SIG-SABR implement the same types of methods and systems. Typically the margins of treatment delivery are adjusted wide enough to accommodate any respiratory motion of a lung tumor. Lung tumor motion is largely driven by diaphragm motion as illustrated in FIGS. 1A and 1B. As illustrated in FIG. 1B, the diaphragm peaks are inspiration and the troughs are expiration where the latter have a lot less motion. The distance between peaks in seconds and their amplitudes in millimeters varies along with base line position shifts. Thus, it can be important to monitor respiratory motion of tumor positions accurately for every breath and for every fraction of treatment dose delivered. Otherwise significant portions of healthy surrounding lung tissue and bone are needlessly damaged by the heavy radiation treatment dose intended only for the malignant tumor itself. Note, in FIG. 1A, the relative position shift of the center of the tumor (the dot) relative to the ribs in Fraction A versus Fraction B.

Figure 2B:
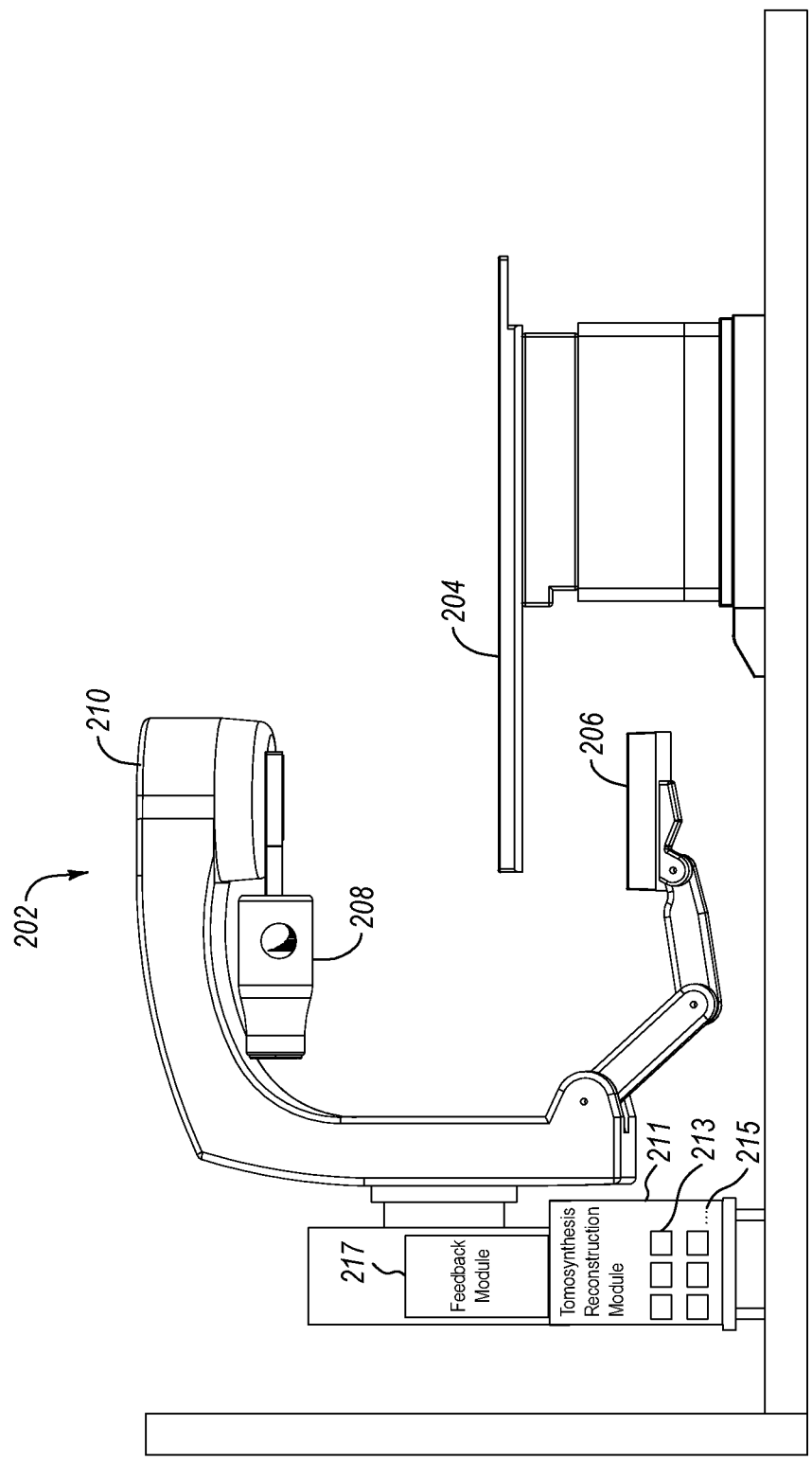
FIG. 2B illustrates an alternate view of a radiotherapy system.

One system that enables the new SIG-SBRT method is illustrated in FIGS. 2A and 2B. A standard rotating C-arm MV linac radiotherapy system 202 is shown with its patient positioning support table 204. A portal X-ray imager panel 206 is opposite a gantry treatment head 210 to help monitor the patient and tumor positions for set up and during treatment. The illustrated embodiment can be conceptualized as a standard MV portal imager but, turned upside down to convert it into a universal kV-MV portal imager. Embodiments may also include a kV multi-source eBeam X-ray tube 208 mounted directly under the MV linac gantry head 210.

Treatment Head

As shown in FIGS. 3A, 3B 3C, and 3D, the X-ray tube 208 has a squared "U" shaped head 212 surrounding the MV linac treatment beam and provides 19 (or some other appropriate number) kV X-ray focal spots (e.g. one focal spot is called out at 214) that illuminate the universal portal imager in the same beams-eye-view (BEV) as the MV treatment beam.

In the illustrated example, the portal X-ray imager panel 206 may be implemented using a flat panel detector available from Varian Medical Systems of Palo Alto, Calif. FIGS. 3A, 3B 3C, and 3D show one example design of a U-shaped eBeam scan tube for the tumor tracking project assuming a conventional radiotherapy gantry system 202 and the Varian portal detector. The eBeam X-ray tube head 212, in this example, is similar in size to the imager panel in that it has dimensions of 30 cm×30 cm and as such is a bit smaller than the Varian MV-kV flat panel detector implemented as the imager panel 206 which is 30 cm×40 cm. This geometry provides a two dimensional scan with a typical tomographic angle of 26 degrees depending with the Source to Detector Distance (SSD) at approximately 150 cm. The electron gun and deflection system may be configured using components that operate at 180 kV. Such an electron gun could be made using suitable parts from L-3 Communications electron devices division. However, this is somewhat longer and larger than what is required here, 120 kV. This part may be a sealed system without active vacuum pumping and contains a mod-anode that serves as a grid for current control. Some embodiments may implement a lighter and more compact system for 130 kV.

The X-ray target of this tube is U-shaped with about an 8-10 degree target angle with respect to the flat panel detector 206 so that the length of the focal spot is shortened by a large factor. The target is made of water cooled copper with thin tungsten braised on the surface. Additional water cooling channels cool the X-ray window and nearby vacuum chamber walls. The eBeam focal spot on the target is in the range of about a 1 mm by 10 mm ellipse for an effective focal spot size of approximately 1 mm FWHM. Beam focusing and steering can be accomplished using a deflection system that employs a solenoid, x-y dipoles, and x-y quadrupoles. An X-ray tuning system is used for beam alignment.

The three straight lengths of the target, in the illustrated example, each have 6 target positions, and with two additional target positions near the two corners, embodiments may have a total of about 20 tomographic views (19 to be precise in the illustrated example). Each target position has an associated collimator to block X-ray paths that fall outside the flat panel detector panel to minimize both patient exposure and scattered radiation. Some embodiments may implement one or more vane collimators inside the vacuum chamber.

Figure 3A:
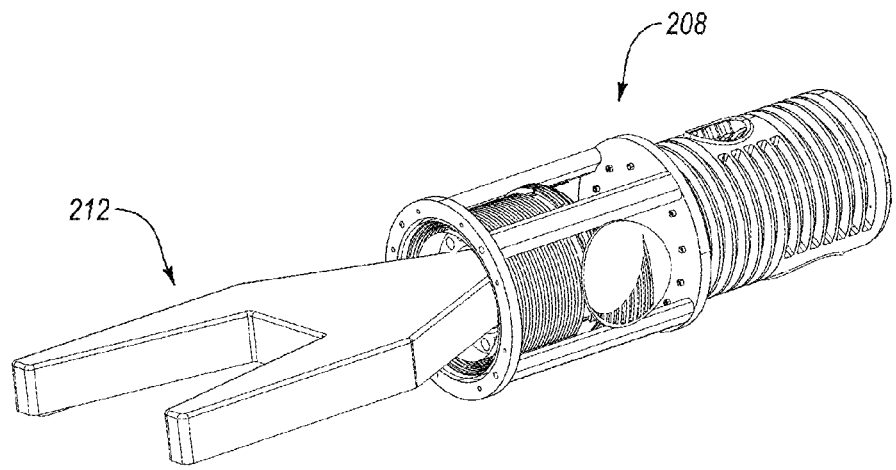
FIG. 3A illustrates an example of an X-ray tube.
Figure 3B:
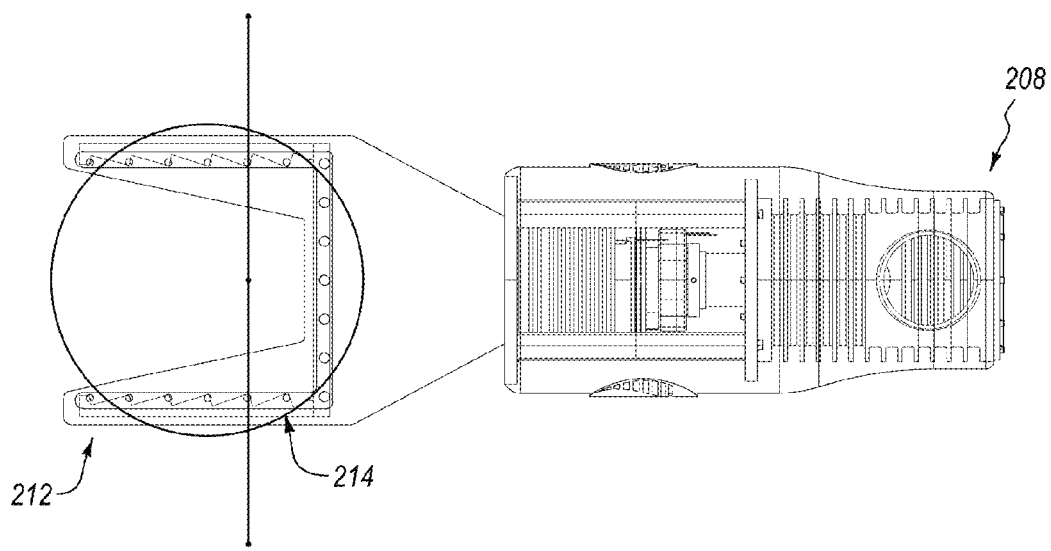
FIG. 3B illustrates an alternate view of the X-ray tube.
Figure 3C:
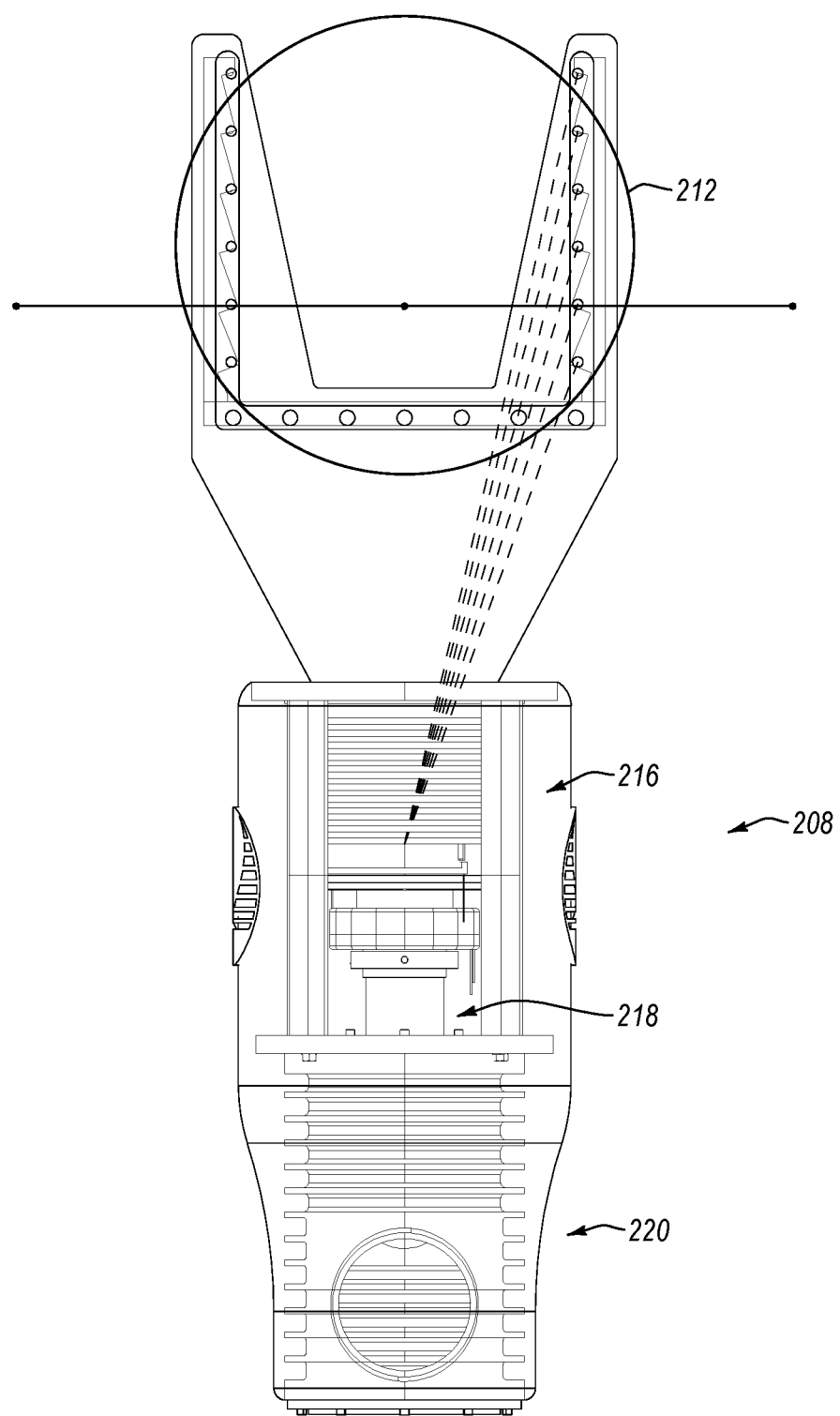
FIG. 3C illustrates yet another alternate view of the X-ray tube.

FIG. 3C illustrates 3D details of the target design and collimator design. This design has 19 target positions. Starting from the top, there is the U configuration of targets and collimator holes. At the center are deflection coils 216 including dipoles, quadrupoles, and a solenoid 218. At the bottom is an electron gun source 220 operating at 50 mA and 130 kV. The gun current is turned on and off using a mod anode.

The kV multi-source eBeam X-ray tube 208 is capable of operating at power levels of 100 mA or higher at up to 180 kV with a duty factor of 50% or higher. However, the portal X-ray imager panel 206 used for imaging is able to operate in the path of the MV treatment beam and recover quickly from saturation produced by MV treatment pulses. For example, the performance of the presently available Varian MV-kV flat panel detector available from Varian Medical Systems of Palo Alto, Calif. limits the speed of the system today to about 2 sec sampling.

Based on various scientific studies and observations, it appears that 10 mAs is sufficient for a high diagnostic quality tomogram of the chest. Further, about 20 views appears to be sufficient, therefore each view would be at about 0.5 mAs. Additionally, applying compressed sensing a further factor of about 10 is feasible.

Some embodiments of the invention can produce near-CT-quality images in planes through the treatment region that are transverse to the therapy beam. Therefore, embodiments can provide real time adjustments to the (multi-leaf collimator) MLC that adjusts the cross section of a therapy beam used applied to a tumor to better conform to the tumor outline (focus treatment beam on the tumor). If the tumor is moving, as is typical in lung cancer, the adjustments will be made in real time during a rotational therapy procedure. This will enable a substantial reduction in the volume of healthy tissue (the margins) that is exposed to radiation thus reducing the volume of non-malignant necrosis.

As illustrated above a unique kV multi-source eBeam X-ray tube 208, which is a scanning electron beam tube that provides rapid switching of an X-ray focal spot in sequence from 19 target sites (or some other appropriate number) positioned along three sides of a square is implemented. This arrangement of focal spots nearly surrounds the MLC near a therapy radiation head 210. A collimator system comprising a tantalum plate with machined apertures just below the targets collimates the X-ray beams such that the universal kV-MV imager 206 can receive each of the 19 projection images in sequence. Since the array of focal spots is offset, the projection images will expose only ½ or less of the rows of pixels in the imager as the projection image moves to different sub-regions on the panel. The readout time for kV imaging on the available imagers is typically 40 msec to 80 msec for the full panel using 2×2 pixel binning. Since only half of the panel need be readout, the readout time per projection image can be reduced to about 20 msec in some embodiments. Prior to reading out, the panel will be exposed to X-rays from a 87 mA, 130 kV electron beam (or other appropriate electron beam) directed on an inclined, water-cooled, tungsten target focused to an effective focal spot size of about 1.4 mm full-width half maximum (FWHM). As noted above the beam can be formed and steered using an X-ray tube that includes components originally developed at Imatron, Inc. for cardiac EBCT, but later improved at L-3 Communications for the development of an airport luggage scanner. The multi-source e-beam X-ray tube is a baked and sealed system maintained with a small electronic Vac-Ion pump.

A unique feature of the universal kV-MV imager 206 is its ability to also record images from the therapy beam. This is feasible since the normal MV copper buildup plate can be placed on the back side of the imager 206, and a forward bias applied to clear a prior image from MV therapy beam exposure in a time interval of 75 msec, for high sensitivity kV imaging, that includes non-linear lag corrections. Although currently available kV-MV imagers with these features are smaller (30 cm×40 cm), larger MV hardened panels for MV imaging of up to 43 cm×43 cm are available and future modifications for dual kV-MV use are feasible.

The basic design parameters for one example system are presented in the table below:

| Specifications | Estimated result | Notes |
| --- | --- | --- |
| X-ray power | 11.6 mAs | 130 kV, 87 mA, 7 msec dwell time, 1.4 mm focal spot size (FWHM), 19 focal positions per scan, 0.6 mAs per spot |
| Resolution | Contour determination estimated at ± 1 mm | 20 1-cm thick slices with 200 × 200 1 mm pixels per slice |
| kV image acquisition time | 513 msec | 27 msec for readout of partial area of panel for each spot (20 msec for readout of half of the panel +7 msec dwell time) |
| Reconstruction time | 200 msec | Iterative reconstruction on GPU followed by tumor contour determination. The MLC will contribute additional latency but can be pre-adjusted by predictive techniques during kV acquisition. |
| Repetition rate | 1 volume image/sec | This assumes 487 msec is used for radiotherapy which is a duty factor of 49%. |
| Tomographic angle | 26° to 32° | Source to isocenter = 64.2 cm, Isocenter to detector = 40 cm, Detector panel size = 43 cm × 43 cm |

Imager Panel

The Varian MV-kV flat plate imager has the following characteristics:

| Property | Spec | Comment |
| --- | --- | --- |
| Readout Time | 67 msec | 15 frames/s |
| Recovery after MV pulse | 67 msec | |
| DQE | 50% | |
| Resolution | .8 × .8 mm pixels | Based on 2 × 2 |
| Size | 30 × 40 cm | |

The system illustrated can be used to acquire images and deliver treatment pulses to a patient. In particular, embodiments may interleave MV pulses (e.g. from an appropriate radio therapy source, such as a linear accelerator, gamma sources, proton sources, carbon ions, etc. in the treatment head 210) and kV pulses (e.g. from the multisource scanning eBeam X-ray tube). Since the recovery time from an MV pulse is relatively long, embodiments may implement a gating scheme with time for MV pulses and kV pulses shared at 50%. Since, in one example embodiment, it will take 20*67 msec=1.34 s to gather about 20 views of kV data, the MV pulsing could be on for about 1 sec followed by about 0.067 recovery and about 1.34 sec of kV imaging. Thus there would be a new tomographic image every 2.4 seconds. The kV imaging readout time could also be speeded up by ×2 reading a reduced area of the portal detector or by summing more pixels, say 3×3 rather than 2×2. In this case performance would be faster as shown. The following table illustrates various detector modes and timing for some embodiments of the invention:

| Detector Mode | kV speed | MV pulsing (s) | MV recovery (s) | kV pulsing (s) | Total Latency (s) | MV duty factor |
| --- | --- | --- | --- | --- | --- | --- |
| Standard Mode | 15/s | 1 | .067 | 1.34 | 2.4 | .42 |
| 2X Mode | 30/s | .5 | .067 | .67 | 1.24 | .40 |
| 3X Mode | 45/s | .45 | .067 | .45 | 0.97 | .46 |
| 6X Mode | 90/s | .23 | .067 | .23 | 0.53 | 0.43 |

This table can be easily adjusted to make the MV duty factor in the range of 40-50% in order to reduce the impact on total treatment time. To achieve latency in the 1 sec range may require a 2-3× speed up of the kV readout. It should be noted that the MV duty factor will in many cases extend the length of time for the therapy treatment.

Figures 3D, 4:
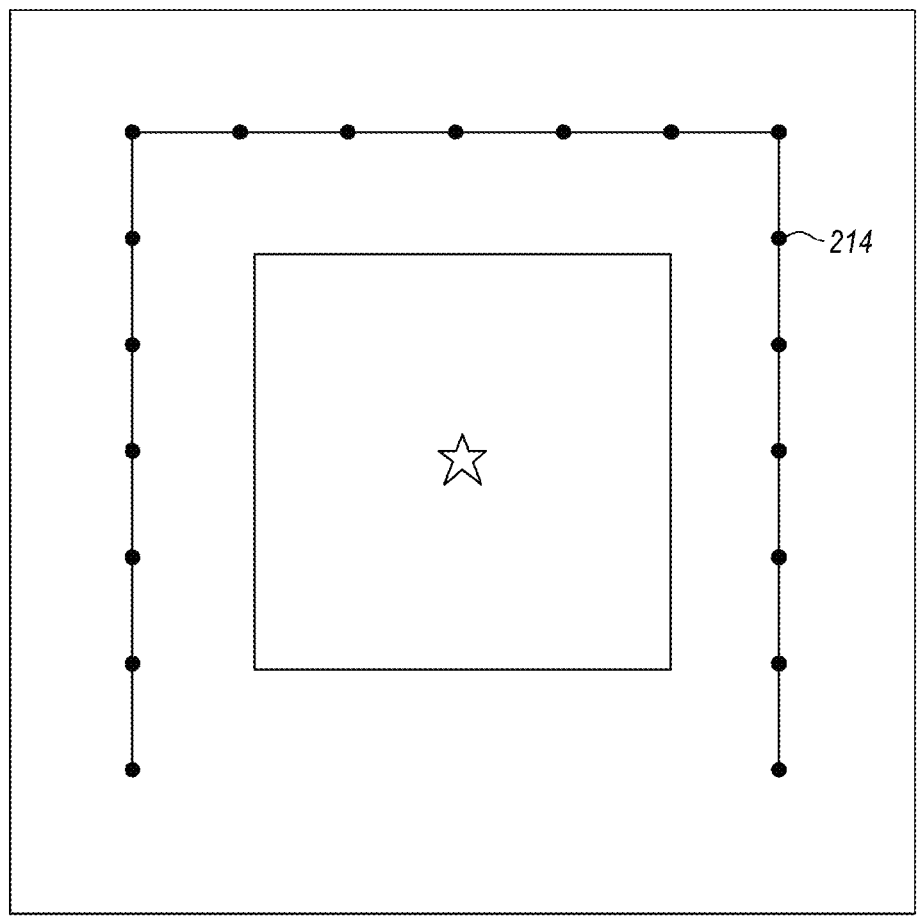
FIG. 3D illustrates a representation of target locations on the X-ray tube.
FIG. 4 illustrates a timing diagram showing timing for actions in a treatment scenario.

In one example embodiment, 19 kV projection images are promptly reconstructed into digital tomosythesis (DTS) images of the lung using a tomosythesis reconstruction module. Such a module may include various computer hardware and logic (such as programmatic or hardware means) to construct appropriate images as explained in more detail below. An example, of the time sequencing of this whole tracking and MV treatment delivery process is summarized in FIG. 4. In particular, FIG. 4 illustrates a 1.92 s cycle time. FIG. 4 illustrates that embodiments acquire 19 kV projection images where each image is performed with a 40 ms readout, plus a 0.7 ms dwell for a total of about 0.89 seconds for all 19 images. MV treatment pulses are delivered for about 0.96 seconds, and a reset for kV imaging is performed for about 0.070 seconds, for a total of about 1.92 seconds per cycle.

The 0.89 s of 19 kV projection image acquisition is synchronized to lie during the least motion, exhale portion of the respiratory cycles shown in FIG. 1B and the 0.96 s fraction dose delivery is synchronized for the next following exhale portion of the cycle to achieve most accurate delivery of a dose centered on the tumor itself. Should an exhale portion occasionally become too short, the kV acquisitions and/or the fraction treatment deliveries can be split between two or more adjacent exhale portions of the cycles. The much larger intensities of the MV treatment beams use a 0.07 s forward bias reset of the universal imager to regain the lower sensitivity needed for the next following kV image acquisition.

Some embodiments have a system latency of about 0.21 s for the multi-leaf collimator of the linac radiotherapy system to adjust its fingers to deliver the fraction dose shape to a new position of the tumor determined by the latest kV DTS image data set. The time between exhales is sufficient to accommodate this multi-leaf collimator repositioning. If the patient respiratory rate changes significantly the dose fraction delivery can be delayed until respiration returns to typical levels. This is what is meant as used herein by "respiratory synchronized image guided SBRT or SABR."

The "Beam's Eye View" (BEV) configuration described above may offer, in some embodiments, at least two innovative benefits. First, DTS volume reconstruction produces relatively poor resolution in the axial dimension, or the direction perpendicular to the motion of the source. Using the BEV configuration, this axis is coincident with the therapy beam axis, and resolution in this direction is not important. Thus an advantage that may be achieved using the BEV geometry is that the resulting tomograms are automatically aligned with the plane of the collimator and its 2-D beam profile impinging on the tumor outline. This alignment is not available using the usual onboard fluoroscopy system that is normally positioned at a large angle to the therapy beam axis. Second, the reconstructed tomograms will have the same physical alignment as the portal MV projection image, and thus will provide a detailed record, or even real-time feedback of the therapy beam profile (e.g. using feedback module 217 of FIG. 2B) with respect to the tumor profile at each gantry angle.

Assuming the X-ray technical factors and timing factors as illustrated above in the example table, a few complete system options may be implemented as follows:

| Detector mode | Detector readout time (msec) | Latency (s) | mA at 130 kV | kV pulse length per view (msec) | kV duty factor | Comments |
|---|---|---|---|---|---|---|
| Standard | 67 | 2.4 | 50 | 10 | .08 | Based on 15/s performance and .067 recovery for today's system |
| 2X | 33 | 1.24 | 50 | 10 | .16 | |
| 3X | 22 | .97 | 50 | 10 | .21 | |
| 6X | 11 | .53 | 50 | 10 | .37 | |

In these modes the eBeam scan tube 208 has grid control enabling shutting down the beam current between pulses. In between pulses the deflection system moves the beam position to the next of about 20 focal spots (in the illustrated example, 19) on the U-track.

The detector performance has little to do with the instantaneous heating of tungsten. Since the tungsten is water cooled, there is typically 0.53-2.4 sec between pulses at the same source spot, which will give ample time for cooling. In this system, water cooling may include cooling of the region around the X-ray window and surrounding vacuum chamber to remove heat due to back scattered electrons in addition to the target.

A further factor of 10 reduction in cooling is feasible based on Compressive Sensing (CS) algorithms, but at a cost of more GPU computing requirements. Part of this factor of 10 will be for abdomen-pelvis imaging due to the greater attenuation in this part of the body as compared to the chest.

It is desirable that the kV radiation exposure be a small fraction of the treatment exposure. Using an X-ray mAs that is 2.3 times an AP chest exposure, and a AP chest skin dose that is 0.04 mSv, embodiments may exhibit approximately 0.1 mSv for each complete scan. Thus the procedure dose will be as follows:

| Detector Mode | Treatment time of 1 min (mSv) | Treatment time of 2 min (mSv) |
|---|---|---|
| Standard | 2.5 | 5 |
| 2x | 4.84 | 9.68 |
| 3X | 6.2 | 12.4 |
| 6X | 11.3 | 22.6 |

Given that the therapy exposure is in the range of 4000-8000 mSv, all of these exposures are well within 1% of treatment exposure.

In conventional tomosyntheis, reconstruction is performed by simple backprojection, sometimes referred to a step and add. However some embodiments use an advanced algorithm based on the theory of Compressive Sensing (CS) Framework. For example, embodiments may use the algorithm described in Andersen, A. H., and A. C. Kak. "Simultaneous algebraic reconstruction technique (SART): a superior implementation of the ART algorithm." Ultrasonic imaging 6.1 (1984): 81-94 or Sidky, Emil Y., et al. "Enhanced imaging of microcalcifications in digital breast tomosynthesis through improved image-reconstruction algorithms." Medical physics 36.11 (2009): 4920-4932, both of which are incorporated herein by reference in their entireties.

Further CS optimizes the signal to noise in the final image enabling dose reduction (or mAs) reduction of up to a factor of 10. However, the CS methods involve iterative reconstruction that is demanding on computer resources. In some embodiments, tomosynthesis reconstruction module 211 may implement the algorithm on graphical processing unit (GPU) boards which have more than 2000 processors 213 in parallel, and using a small array of these boards embodiments can achieve volume tomosynthesis reconstruction times in the fractions of a second. More or fewer processors 213 may be used, as indicated by ellipses 215. Further, embodiments may implement fast image segmentation of this GPU array, and the image segmentation will enable fast boundary detection to be delivered to the multi-leaf collimator system of the radiotherapy gantry. In particular, some embodiments may use NVidia GPU cards for image reconstruction as part of the tomosynthesis reconstruction module, in place of other computing system computer. Algorithms may be coded using CUDA, the native language for NVidia GPUs or OpenCL available from khronos.org.

Figure 5:
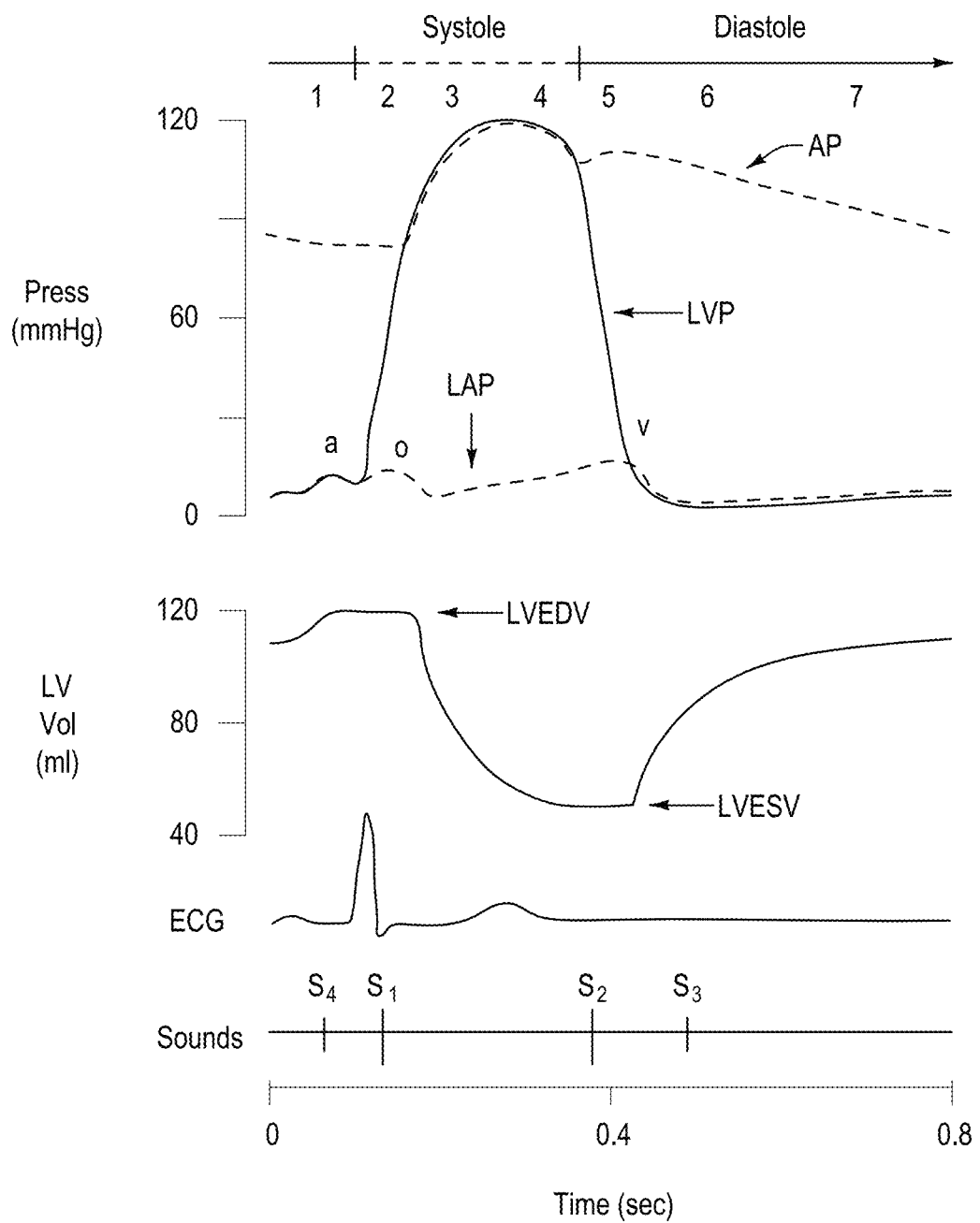
FIG. 5 illustrates a representative cardiac cycle.

One alternate embodiment adds cardiac synchronization to SIG-SBRT and SIG-SABR. The normal resting heart rate is 60 to 100 beats per min. This corresponds to a heartbeat every 0.6 to 1.0 s. A representative cardiac cycle is shown in FIG. 5. The minimum heart beat driven motion of lung tumors is during the Regions 1, the last half of 6 and 7 of the diastole portion of the pressure cycle of the heart beat and just before the EGG peak that initiates each heart beat where the volume change is the lowest. For cardiac synchronized SIG-SBRT and SIG-SABR or lung tumors the 19 images are still taken during the exhale portions of the respiratory cycles but are delayed unless they also correspond to the diastole Regions 1, half of 6 and 7 of the cardiac cycle. This will inevitably spread the 19 kV projection image acquisitions over 2 or 3 or more respiratory cycles, correspondingly lowering the overall accuracy but still much better than previous systems that have to have margins that encompass all respiratory and cardiac motion that includes substantial damage to a lot of healthy tissue and bone.

Another alternate or additional feature of embodiments increases the frame rate of the kV images acquisition to 600 fps and lowers the dwell time for each focal spot to 1.7 ms for the multi-source kV e-Beam X-ray tube 208. This substantially lowers the acquisition time for the 19 kV projection images and speeds up the radiotherapy fraction delivery cycle to as high as 1.87 cycles per second. This means that the DTS image acquisition can be a short as one respiratory cycle (depending on synchronization with cardiac rates) so that motion tracking, MLC latency and treatment fraction delivery can be as short and as accurate as two respiratory cycles allows. This depends on several factors including the sufficient computer speeds required for fast DTS image reconstruction in the corresponding limited time, the DTS images still being of "tracking quality" even though the mAs from the e-Beam kV X-ray tube 208 will be corresponding less than when a 7 ms dwell time is used, and finally on the availability of a radiation hard, amorphous silicon X-ray imager that can operate at 600 fps.

Another alternate or additional feature of some embodiments is to use a full sized amorphous silicon flat panel portal imager, such as one 43×43 cm in active area, but only readout a reduced region-of-interest (ROI) so as to achieve or 600 fps or higher imaging rates.

Another alternate or additional feature of some embodiments may use the embodiments described above to track tumor motion in multiple other sites in the body during radiothearapy where motion management is a problem.

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 6:
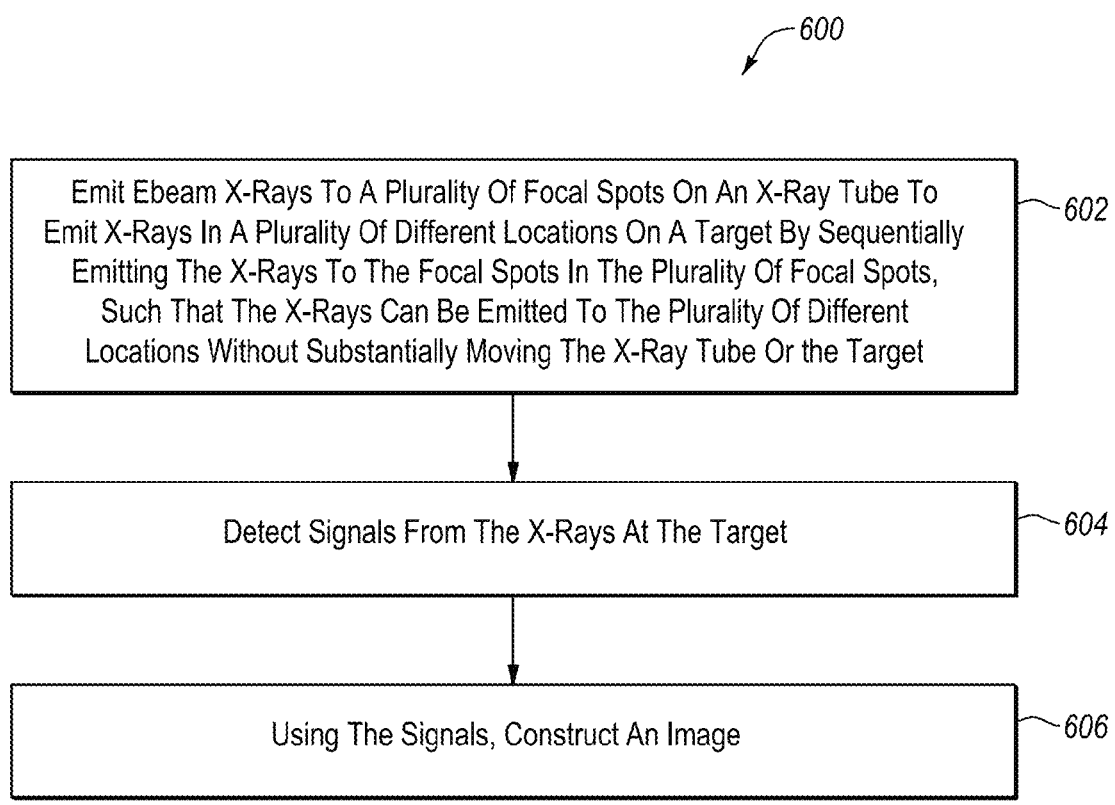
FIG. 6 illustrates a method of tracking tumors during radiotherapy.

Referring now to FIG. 6, a method 600 is illustrated. The method 600 includes acts for tracking tumors during radiotherapy for interleaving treatment pulses with imaging pulses. The method 600 includes emitting ebeam x-rays to a plurality of focal spots on an x-ray tube to emit x-rays in a plurality of different locations on a target by sequentially emitting the x-rays to the focal spots in the plurality of focal spots, such that the x-rays can be emitted to the plurality of different locations without substantially moving the x-ray tube or the target (act 602). The method 600 further includes detecting signals from the x-rays at the target (act 604). Using the signals, an image is constructed (act 606).

The method 600 may be practiced where emitting eBeam X-rays to a plurality of focal spots on an X-ray tube comprises emitting eBeam X-rays to 19 spots on the X-ray tube.

The method 600 may be practiced where constructing the image comprises processing detected signals using one or more GPUs.

The method 600 may be practiced where the method is performed by sequentially emitting the X-rays to all the focal spots in one respiratory cycle of a patient being treated.

The method 600 may be practiced where emitting eBeam X-rays to a plurality of focal spots on an X-ray tube to emit X-rays in a plurality of different locations on a target is synchronized with a cardiac cycle of a patient being treated.

The method 600 may be practiced where the method is performed to achieve an image acquisition rate of 600 fps.

The method 600 may be practiced where emitting eBeam X-rays comprises emitting X-rays of no more than 130 kV.

What is claimed is:

1. A system for tracking tumors during radiotherapy by delivering treatment pulses along with imaging pulses, the system comprising:

a radiotherapy device configured to provide the treatment pulses in at least one treatment beam;

a multisource scanning eBeam X-ray tube having a plurality of focal spots, the X-ray tube being configured to emit the imaging pulses including X-rays from a plurality of different stationary, discrete locations on a target by sequentially emitting the X-rays from the plurality of focal spots of the X-ray tube;

an imager panel configured to act as a detector and configured to receive the X-rays from the focal spots of the X-ray tube; and a tomosynthesis reconstruction module configured to process a plurality of sequential outputs from the imager panel to construct a combined tomosynthesis image based on the plurality of sequential outputs, wherein the imaging pulses are delivered along with the treatment pulses provided by the radiotherapy device;

wherein the multisource scanning eBeam X-ray tube is substantially next to the treatment beam and provides the plurality of focal spots that illuminate the imager panel so that images are reconstructable in substantially the same beams-eye-view as the treatment beam; and wherein the multisource scanning eBeam X-ray tube sequentially scans each of the plurality of stationary, discrete locations on the target for a specified period of time before moving to the next discrete location on the target, wherein the imaging pulses are cycled off between each discrete location, allowing the imager panel to be read out in a synchronous manner between each scan in the cycle.

2. The system of claim 1, wherein the multisource eBeam X-ray tube comprises a U shaped head having the plurality of focal spots.

3. The system of claim 1, wherein the multisource eBeam X-ray tube comprises 19 focal spots.

4. The system of claim 1, wherein the tomosynthesis reconstruction module comprises a GPU having at least 2000 processors working in parallel.

5. The system of claim 1, wherein the tomosynthesis reconstruction module comprises a plurality of GPUs, each GPU having at least 2000 processors working in parallel.

6. The system of claim 1, wherein the system is configured to emit X-rays in the plurality of different locations on the target by sequentially emitting the X-rays from all the focal spots in a fraction of one respiratory cycle of a patient being treated.

7. The system of claim 1, wherein the eBeam X-ray tube is configured to emit X-rays of no more than 130 kV.

8. A method for tracking tumors during radiotherapy by delivering treatment pulses along with imaging pulses, the method comprising:

providing the treatment pulses in at least one treatment beam;

emitting eBeams to a plurality of focal spots on a multi-source scanning eBeam X-ray tube to emit the imaging pulses including X-rays from a plurality of different stationary, discrete locations on a target by sequentially emitting the X-rays from the plurality of focal spots of the X-ray tube;

detecting a plurality of subsequent signals from the X-rays at an imager panel; and using the plurality of subsequent signals, constructing a combined tomosynthesis image based on the plurality of sequential outputs, wherein the imaging pulses are delivered along with the treatment pulses provided in the treatment beam;

wherein the multisource scanning eBeam X-ray tube is substantially next to the treatment beam and provides the plurality of focal spots that illuminate the imager panel so that image reconstruction is in substantially the same beams-eye-view as the treatment beam; and wherein the multisource scanning eBeam X-ray tube sequentially scans each of the plurality of stationary, discrete locations on the target for a specified period of time before moving to the next discrete location on the target, wherein the imaging pulses are cycled off between each discrete location, allowing the imager panel to be read out in a synchronous manner between each scan in the cycle.

9. The method of claim 8, wherein emitting eBeams to the plurality of focal spots on the X-ray tube comprises emitting eBeams to 19 focal spots on the X-ray tube.

10. The method of claim 8, wherein constructing the image comprises processing detected signals using one or more GPUs.

11. The method of claim 8, wherein the method is performed by sequentially emitting the X-rays from all the focal spots in one fraction of a respiratory cycle of a patient being treated.

12. The method of claim 8, wherein emitting eBeams to the plurality of focal spots on an X-ray tube to emit X-rays from a plurality of different locations on a target is synchronized with a cardiac cycle of a patient being treated.

13. The method of claim 8, wherein the method is performed to achieve an image acquisition rate of 600 fps.

14. The method of claim 8, wherein the multisource scanning eBeam X-ray tube comprises a single electron beam emitter with one or more deflection coils configured to steer the scanning beam onto a plurality of different locations on the targets.

15. The system of claim 2, wherein the system comprises a tracking x-ray imager system, and wherein the plurality of focal spots of the U shaped head substantially surround the treatment beam.

16. The system of claim 15, wherein the U shaped arrangement of focal spots from the U shaped head are centered a specified of number degrees from the treatment beam direction, such that the U shaped arrangement of focal spots surround the treatment beam.

17. The system of claim 16, wherein the specified number of degrees is between 15 and 60 degrees.

18. The system of claim 15, wherein the system includes at least first and second tracking x-ray imager systems, said first and second tracking x-ray imaging systems each having U shaped arrangements of focal spots, and wherein each of the arrangements of U shaped focal spots are centered a specified number of degrees from the treatment beam direction.

19. The system of claim 1, wherein the combined tomosynthesis image is analyzed to identify a tumor outline, the tumor outline being used as feedback to adjust one or more cross section parameters of the treatment beam in real-time.

* * * * *